Nov. 1, 1955 F. W. ANDERSON Plant Pat. 1,430

NECTARINE TREE

Filed Feb. 4, 1955

WITNESS

Addison J. Avery

INVENTOR

Frederic W. Anderson

Webster & Webster

ATTYS.

United States Patent Office

Plant Pat. 1,430
Patented Nov. 1, 1955

1,430

NECTARINE TREE

Frederic W. Anderson, Merced, Calif.

Application February 4, 1955, Serial No. 486,304

1 Claim. (Cl. 47—62)

This invention relates to a new and distinct variety of nectarine tree originated by me during the course of a continuing experimental program for the development of nectarine varieties having commercially desirable characteristics.

The instant variety of nectarine tree bears white fleshed, semi-freestone, early ripening fruit which is distinct—in comparison to the John Rivers nectarine (unpatented) which is presently the leading nectarine in acreage in California, and heretofore the earliest ripening commercial variety—by a ripening period which is approximately ten days earlier, by somewhat softer flesh, and by much more red exterior color which makes it highly attractive for market use.

In further comparison to the John Rivers nectarine the fruit of the present variety averages slightly smaller in size.

In comparison to the Grand Rivers nectarine (United States Plant Patent 1,248), the fruit here is white fleshed rather than yellow fleshed, and is a few days earlier in ripening.

The present variety of nectarine tree was originated by me in my experimental orchard at Le Grand, California, as an F–2 cross of Le Grand nectarine (United States Plant Patent 549) and said John Rivers nectarine.

When such cross, which was grown under conditions of close inspection and continuing comparison with other varieties, came into bearing I recognized its distinctive features and commercial potential, and therefore selected it for reproduction.

Asexual reproduction of the variety was accomplished by me in my experimental orchard, as aforesaid, by top working—specifically by budding—on mature orchard trees. Such asexual reproductions were found to carry forward all of the characteristics of the parent.

Figure 1:
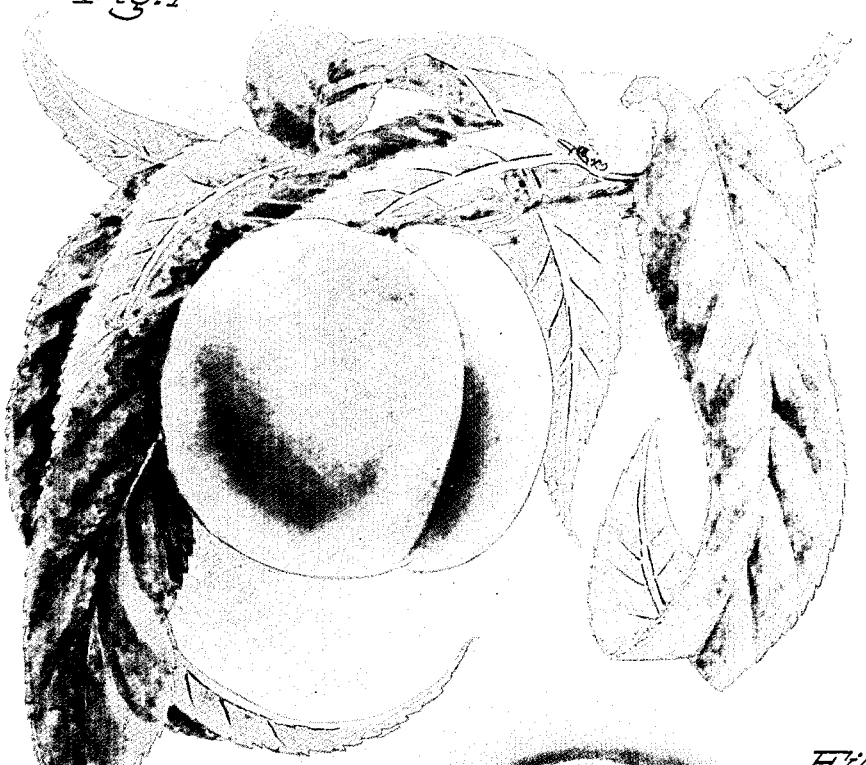
Fig. 1 is an elevation of one of the fruit, together with a twig and leaves.
Figure 2:
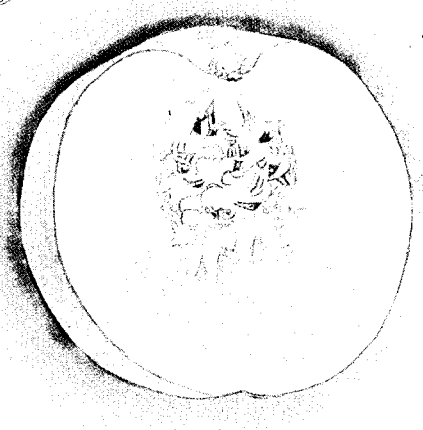
Fig. 2 is a sectional elevation of one of the fruit, with the stone partly exposed.
Figure 3:
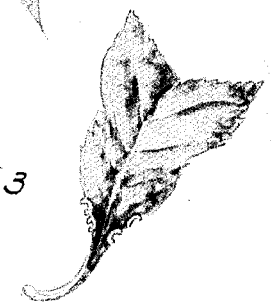
Fig. 3 is a fragmentary elevation of a leaf.

Referring now more specifically to the pomological details of this new and distinct variety of nectarine tree, the following is an outline description thereof; all major color plate identifications being by reference to Maerz and Paul Dictionary of Color:

Tree:
- *Size.*—Medium.
- *Growth.*—Upright to spreading.
- *Production.*—Very productive.
- *Bearing.*—Regular bearer.

Trunk:
- *Size.*—Medium.

Branches:
- *Size.*—Medium.
- *Color.*—Brown.

- *Lenticels.*—Medium number; medium size.

Leaves:
- *Size.*—Medium. Average length — 6"; average width—1⅜".
- *Form.*—Acutely pointed.
- *Thickness.*—Medium.
- *Color.*—Top side—medium green (22–L–9). Under side—lighter green (21–I–6).
- *Margin.*—Crenate.
- *Petiole.*—Medium length; medium thickness.
- *Glands.*—Average number—four. Medium size; reniform. Usually positioned two on petiole, two or more on blade.
- *Stipules.*—None.

Flower buds:
- *Size.*—Medium.
- *Form.*—Conic.

Flowers:
- *Dates of first and full bloom.*—About with the Elberta peach (unpatented). Medium blooming period compared with other varieties.
- *Size.*—Large.

Fruit:
- *Maturity when described.*—Eating ripe.
- *Date of first picking.*—June 10, 1954.
- *Date of last picking.*—June 20, 1954.
- *Size.*—Uniform; medium to small. Average diameter axially—2¼"; average transversely in suture plane—2⅛".
- *Form.*—Symmetrical; globose.
- *Suture.*—Shallow, with slight depression beyond pistil point.
- *Ventral surface.*—Rounded slightly; lips equal.
- *Cavity.*—Elongated in suture plane with suture showing on one side. Average depth—⅜"; average breadth—⅜".
- *Base.*—Oblique.
- *Apex.*—Short; depressed.
- *Pistil point.*—Lacking.

Skin:
- *Texture.*—Medium; tenacious to flesh.
- *Tendency to crack.*—None in wet seasons.
- *Down.*—Wanting.
- *Color.*—Dull yellow (11–L–6), almost completely overspread with a bright red (4–L–6), shading to a darker red (6–L–6).

Flesh:
- *Amygdalin.*—Moderate.
- *Juice.*—Abundant.
- *Texture.*—Medium to soft; melting.
- *Fibers.*—Few; fine.
- *Ripens.*—Even.
- *Flavor.*—Subacid to mild; vinous.
- *Aroma.*—Pronounced.
- *Eating quality.*—Good.
- *Color.*—Whitish (9–B–1, shading to 10–B–2), with a slight purplish tinge (9–A–2) in the portion adjacent the apex.

Stone:
- *Type.*—Semi-free.
- *Size.* — Small. Average length — 1⅛"; average breadth—1"; average thickness—¾".
- *Form.*—Oblong.
- *Base.*—Straight.
- *Hilum.*—Oblong.
- *Apex.*—Rounded.
- *Sides.*—Equal.
- *Surface.*—Regularly furrowed throughout. Ridged throughout.
- *Ridges.*—Rounded.
- *Pits.*—Elongated.

*Ventral edge.*—Thick.
*Dorsal edge.*—Full, with broad groove.
*Tendency to split.*—Slight.
*Color.*—Light brown (11–H–8).
Use: Market; local.
Keeping quality: Medium.
Shipping quality: Medium to poor.

The tree and its fruit herein described may vary in slight detail due to climatic and soil conditions under which the variety may be grown.

The following is claimed:

A new and distinct variety of nectarine tree, as illustrated and described, characterized by white fleshed, semi-freestone, early ripening fruit which—in comparison to the John Rivers nectarine—ripens approximately ten days earlier, is slightly smaller in size and softer in flesh, and with more red exterior color; and characterized—in comparison to the Grand Rivers nectarine—by while instead of yellow flesh, and by a ripening period a few days earlier.

No references cited.